(12) United States Patent
Csurka et al.

(10) Patent No.: US 9,589,231 B2
(45) Date of Patent: Mar. 7, 2017

(54) SOCIAL MEDICAL NETWORK FOR DIAGNOSIS ASSISTANCE

(71) Applicant: Xerox Corporation, Norwalk, CT (US)

(72) Inventors: Gabriela Csurka, Crolles (FR); Florent C. Perronnin, Domène (FR)

(73) Assignee: XEROX CORPORATION, Norwalk, CT (US)

( * ) Notice: Subject to any disclaimer, the term of this patent is extended or adjusted under 35 U.S.C. 154(b) by 424 days.

(21) Appl. No.: 14/263,348

(22) Filed: Apr. 28, 2014

(65) Prior Publication Data

US 2015/0310177 A1    Oct. 29, 2015

(51) Int. Cl.
| | |
|---|---|
| *G06N 5/02* | (2006.01) |
| *G06Q 10/06* | (2012.01) |
| *G06Q 10/10* | (2012.01) |
| *G06N 5/04* | (2006.01) |
| *G06F 19/00* | (2011.01) |

(52) U.S. Cl.
CPC ........... *G06N 5/04* (2013.01); *G06F 19/3443* (2013.01); *G06N 5/02* (2013.01); *G06Q 10/10* (2013.01); *G06N 5/022* (2013.01)

(58) Field of Classification Search
None
See application file for complete search history.

(56) References Cited

U.S. PATENT DOCUMENTS

| | | | |
|---|---|---|---|
| 7,058,567 B2 | 6/2006 | Aït-Mokhtar et al. |
| 2007/0056356 A1 | 3/2007 | Brock |
| 2007/0258648 A1 | 11/2007 | Perronnin |
| 2008/0069456 A1 | 3/2008 | Perronnin |
| 2010/0017225 A1 | 1/2010 | Oakley et al. |
| 2010/0026831 A1 | 2/2010 | Ciuc et al. |

(Continued)

FOREIGN PATENT DOCUMENTS

WO    WO 0209580    2/2002

OTHER PUBLICATIONS

Althoff et al., Agent Based Maintenance for Modularised Case Bases in Collaborative Multi-Expert Systems [online], 2007 [retrieved on Aug. 9, 2016]. Retrieved from the Internet<URL:https://www.uni-hildesheim.de/media/fb4/informatik/AG_IIS/Dokumente-Allgemein/Paper/UKCBR07_AlthoffEtAl.pdf>.*

(Continued)

*Primary Examiner* — Stanley K Hill
*Assistant Examiner* — Nathan Brown, Jr.
(74) *Attorney, Agent, or Firm* — Fay Sharpe LLP (57) ABSTRACT

A method for diagnosis assistance exploits similarity between a new medical case and existing medical cases and experts when embedded in a common embedding space. Different types of queries are provided for, including a query-by-cases and a query-by-experts. These may be associated with different cost structures that encourage the requester to use the query-by-cases first and seek expert assistance if this proves unsuccessful. Depending on whether the query-by-cases or query-by-experts is requested, a subset of the existing cases or experts is identified based on the similarity of their representations, in the embedding space, with a representation of the new case in the embedding space. There may then be provision for communicating the new case to a selected one or more of the subset of experts for the expert to attempt to provide a diagnosis.

22 Claims, 4 Drawing Sheets

(56) References Cited

U.S. PATENT DOCUMENTS

| | | | |
|---|---|---|---|
| 2010/0082615 | A1 | 4/2010 | Clinchant et al. |
| 2010/0092084 | A1 | 4/2010 | Perronnin et al. |
| 2010/0098343 | A1 | 4/2010 | Perronnin et al. |
| 2010/0189354 | A1 | 7/2010 | De Campos et al. |
| 2010/0312798 | A1 | 12/2010 | Dutta et al. |
| 2011/0026831 | A1 | 2/2011 | Perronnin et al. |
| 2011/0040711 | A1 | 2/2011 | Perronnin et al. |
| 2011/0072012 | A1 | 3/2011 | Ah-Pine et al. |
| 2011/0091105 | A1 | 4/2011 | Perronnin |
| 2011/0137898 | A1 | 6/2011 | Gordo et al. |
| 2012/0045134 | A1 | 2/2012 | Perronnin et al. |
| 2012/0054130 | A1 | 3/2012 | Mensink et al. |
| 2012/0060216 | A1 | 3/2012 | Chaudhri et al. |
| 2012/0076401 | A1 | 3/2012 | Sánchez et al. |
| 2012/0078062 | A1 | 3/2012 | Bagchi et al. |
| 2012/0143853 | A1 | 6/2012 | Gordo et al. |
| 2012/0158739 | A1 | 6/2012 | Ah-Pine et al. |
| 2013/0138455 | A1 | 5/2013 | Saharan |
| 2013/0179176 | A1 | 7/2013 | Gotthardt |
| 2013/0204885 | A1 | 8/2013 | Clinchant et al. |

OTHER PUBLICATIONS

U.S. Appl. No. 13/898,805, filed May 21, 2013, Csurka, et al.

Ah-Pine, J., et al., "Crossing textual and visual content in different application scenarios," Multimedia Tools and Applications 42, 1, pp. 31-56 (2009).

Ah-Pine, J., et al., "Comparison of several combinations of multimodal and diversity seeking methods for multimedia retrieval," Multilingual information Access Evaluation II; Multimedia Experiments, LNCS 6242, pp. 124-132 (2010).

Aït-Mokhtar, S., et al., "Robustness beyond Shallowness: Incremental Deep Parsing" Natural Language Engineering 8, pp. 121-144 (2002).

Aït-Mokhtar, S., et al., "Incremental Finite-State Parsing," Proc. $5^{th}$ Conf. on Applied Natural Language Processing, (ANLP'97), pp. 72-79 (1997).

Aït-Mokhtar, S., et al., "Subject and Object Dependency Extraction Using Finite-State Transducers," Proc. $35^{th}$ Conf. of the Association for Computational Linguistics (ACL'97), Workshop on Information Extraction and the Building Lexical Semantic Resources for NLP Applications, pp. 71-77 (1997).

Aladin-Dth, Development of an automated assistant to monitor Hospital Acquired Infections—A Detection System for Hospital Acquired Infections from Patient Discharge Summaries, downloaded at http://www.aladin-project.eu/ on Feb. 21, 2014, pp. 1.

Bodenreider, "The Unified Medical Language System (UMLS): integrating biomedical terminology," Nucleic Acids Research, 32, pp. D267-D270 (2004).

Bozzon, A., et al., Choosing the Right Crowd: Expert Finding in Social Networks, Proc. 16th Intern'l Conf. on Extending Database Technology (EDBT/ICDT), pp. 637-648 (Mar. 2013).

Chowdary, C. R., et al., "Esum: an efficient system for query-specific multi-document summarization." in ECIR (Advances in Information Retrieval), pp. 724-728 (2009).

Cohen, N., "Editing Wikipedia pages for Med School credit," New York Times, published online on Sep. 29, 2013, pp. 1-2, downloaded at http://www.nytimes.com/2013/09/30/business/media/editing-wikipedia-pages-for-med-school-credit.html?smid=fbshare&_r=3&goback=.gde_3745929_member_5791852792284987393& on Feb. 21, 2014.

Csurka, et al., "Unsupervised Visual and Textual Information Fusion in Multimedia Retrieval—A Graph-based Point of View," arXiv:1401.6891v1 [cs.IR] pp. 1-35 (Jan. 27, 2014).

Eurorad, "Radiologic Teaching Files," pp. 1, downloaded at http://www.eurorad.org/ on Feb. 21, 2014.

European Commission, CORDIS Projects: EURECA, "Enabling information re-Use by linking clinical REsearch and Care," pp. 1-2 (Jan. 16, 2012).

Frantziy, K., et al., "Automatic Recognition of Multi-Word Terms: the C-value/NC-value Method," Intern'l J. on Digital Libraries. 3, 2, 115-130 (2000).

Google, "Medical condition & symptom search," pp. 1-3, downloaded at https://support.google.com/websearch/answer/2364942?hl=en&p=g_symp&goback=.gde_3745929_member_166739157#! on Feb. 21, 2014.

Hagège C., et al., "Linguistic and Temporal Processing for Discovering Hospital Acquired Infection from Patient Records," Proc. KR4HC, ECAI 2010, pp. 70-84 (Aug. 2010).

Haghighi, A., et al., "Exploring Content Models for Multi-Document Summarization," ACL NAACL '09: Proceedings of Human Language Technologies: The 2009 Annual Conference of the North American Chapter of the Association for Computational Linguistics, pp. 362-370, ACL (2009).

HIFA 2015, A global campaign: Healthcare Information for All by 2015, pp. 1-4 downloaded at http://www.hifa2015.org/about/why-hifa2015-is-needed/ on Feb. 21, 2014.

MyPACS, "Teaching Files: About MyPACS," pp. 1-2, downloaded at www.mypacs.net/ on Feb. 21, 2014.

Noll, M.G., et al., "Telling Experts from Spammers: Expertise Ranking in Folksonomies," SIGIR'09, pp. 612-619 (2009).

One Million Healthcare Workers Campaign, pp. 1-7, downloaded at http://1millionhealthworkers.org/about-us/ on Feb. 21, 2014.

OzmosisESP, pp. 1-3, downloaded at http://ozmosis.com/solutions/health-systems/ on Feb. 20, 2014.

PatientsLikeMe, pp. 1-3 downloaded at http://www.patientslikeme.com/, on Feb. 20, 2014.

Patwardhan, S., et al., "Using WordNet-based context vectors to estimate the semantic relatedness of concepts," Proc. EACL 2006 workshop, Making sense of sense: Bringing computational linguistics and psycholinguistics together, Trento, Italy, pp. 1-8 (2006).

Pedersen, T., "Measuring the Similarity and Relatedness of Concepts in the Medical Domain: IHI 2012 Tutorial," pp. 1-210 (2012) downloaded at http://www.comp.hkbu.edu.hk/ihi2011/Documents%20-%20web2011IHI_files/IHI2012-semantic-similarity-tutorial.pdf on Feb. 21, 2014.

Pedersen, et al., "Measures of Semantic Similarity and Relatedness in the Biomedical Domain," J. Biomedical Informatics 40: 288-299 (2007).

Perronnin, et al., "Fisher Kernels on Visual Vocabularies for Image Categorization," Computer Vision and Pattern Recognition (CVPR), pp. 1-8 (2007).

Sermo, "Who we are," pp. 1-2, downloaded at http://www.sermo.com/about/who-we-are on Feb. 20, 2014.

Shen, C., "Multi-Document Summarization via the Minimum Dominating Set," COLING, pp. 984-992 (2010).

Tang, J., "ArnetMiner: extraction and mining of academic social networks" Proc. 14th ACM SIGKDD international conference on Knowledge discovery and data mining, pp. 990-998 (2008).

Tominski, C., et al., "TimeViz Browser—A Visual Survey of Visualization Techniques for Time-Oriented Data," pp. 1-6 (Nov. 28, 2013), available at http://survey.timeviz.net/.

Tsukayama, H., "Watson, the 'Jeopardy!' computer, has grander plans," Washington Post, Post Tech, posted Feb. 16, 2011, pp. 1-4, downloaded at http://voices.washingtonpost.com/posttech/2011/02/watson_the_jeopardy_computer_h.html on Feb. 21, 2014.

\* cited by examiner

SOCIAL MEDICAL NETWORK FOR DIAGNOSIS ASSISTANCE

BACKGROUND

The exemplary embodiment relates to medical diagnosis and finds particular application in connection with a system and method for providing different levels of assistance to healthcare workers for medical diagnosis.

Many people suffer from a variety of preventable and treatable medical conditions, such as diseases. In part, this is because patients, caregivers, and health workers do not have access to the information and knowledge they need, when they need it, to make appropriate decisions and thus provide appropriate treatment. Many health workers could be more effective when supported by a clinically-skilled health workforce. However, the number of clinically skilled health workers is limited, especially in very specific domains and in some locations.

Recently, social medical platforms have been developed which facilitate the exchange of information between users, and in particular, between medical practitioners. In some cases, users can ask for help or advice from others. For example, medical practitioners are able to share photographs, laboratory test results, imaging results, EKG data, and the like, so that other practitioners can contribute to the diagnosis. However the number of experts that are specialists in a given field and the time they have available to assist other practitioners is often limited, when compared to the number of cases for which help is needed.

There remains a need for a system and method that can provide health workers with information to assist them in making a diagnosis by providing access to information and experts using a common query interface.

INCORPORATION BY REFERENCE

The following references, the disclosures of which are incorporated herein by reference in their entireties, are mentioned:

The following relate to medical diagnosis: WO 2002009580, entitled ONLINE MEDICAL EVALUATION AND TREATMENT SYSTEM, METHOD AND PORTAL, to Healthshore, Inc.; U.S. Pub. No. 20100017225, published Jan. 21, 2010, entitled DIAGNOSTICIAN CUSTOMIZED MEDICAL DIAGNOSTIC APPARATUS USING A DIGITAL LIBRARY, by David Oakley, et al.; U.S. Pub. No. 20100312798, published Dec. 9, 2010, entitled RETRIEVAL OF SIMILAR PATIENT CASES BASED ON DISEASE PROBABILITY VECTORS, by Pradyumna Dutta, et al.; U.S. Pub. No. 20120060216, published Mar. 8, 2012, entitled MEDICAL INFORMATION NAVIGATION ENGINE (MINE) SYSTEM, by Imran N. Chaudhri, et al.; U.S. Pub. No. 20120078062, published Mar. 29, 2012, entitled DECISION-SUPPORT APPLICATION AND SYSTEM FOR MEDICAL DIFFERENTIAL-DIAGNOSIS AND TREATMENT USING A QUESTION-ANSWERING SYSTEM, by Sugato Bagchi, et al.; U.S. Pub. No. 20130138455, published May 30, 2013, entitled AUTOMATED INTEGRATED SYSTEM, METHOD AND PLATFORM FOR HEALTHCARE SERVICES, by Pawan Saharan; and U.S. Pub. No. 20130179176, published Jul. 11, 2013, entitled COMPUTER IMPLEMENTED METHOD FOR DETERMINING THE PRESENCE OF A DISEASE IN A PATIENT, by Frank Gotthardt.

U.S. application Ser. No. 13/898,805, filed May 21, 2013, entitled TARGETED SUMMARIZATION OF MEDICAL DATA BASED ON IMPLICIT QUERIES, by Gabriela Csurka, et al., describes a framework for representing medical data.

The following relate generally to methods for generation of representations of image data: U.S. Pub. No. 20100082615, published Apr. 1, 2010, entitled CROSS-MEDIA SIMILARITY MEASURES THROUGH TRANS-MEDIA PSEUDO-RELEVANCE FEEDBACK AND DOCUMENT RERANKING, by Stéphane Clinchant, et al.; U.S. Pub. No. 20110026831, published Feb. 3, 2011, entitled COMPACT SIGNATURE FOR UNORDERED VECTOR SETS WITH APPLICATION TO IMAGE RETRIEVAL, by Florent Perronnin, et al.; U.S. Pub. No. 20110040711, published Feb. 17, 2011, entitled TRAINING A CLASSIFIER BY DIMENSION-WISE EMBEDDING OF TRAINING DATA, by Florent Perronnin, et al.; U.S. Pub. No. 20110072012, published Mar. 24, 2011, entitled SYSTEM AND METHOD FOR INFORMATION SEEKING IN A MULTIMEDIA COLLECTION, by Julien Ah-Pine, et al.; U.S. Pub. No. 20110091105, published Apr. 21, 2011, entitled BAGS OF VISUAL CONTEXT-DEPENDENT WORDS FOR GENERIC VISUAL CATEGORIZATION, by Florent Perronnin; U.S. Pub. No. 20110137898, published Jun. 9, 2011, entitled UNSTRUCTURED DOCUMENT CLASSIFICATION, by Albert Gordo, et al.; U.S. Pub No. 20120045134, published Feb. 23, 2012, entitled LARGE SCALE IMAGE CLASSIFICATION, by Florent Perronnin, et al.; U.S. Pub No. 20120054130, published Mar. 1, 2012, entitled RETRIEVAL SYSTEMS AND METHODS EMPLOYING PROBABILISTIC CROSS-MEDIA RELEVANCE FEEDBACK, by Thomas Mensink, et al., U.S. Pub No. 20120076401, published Mar. 29, 2012, entitled IMAGE CLASSIFICATION EMPLOYING IMAGE VECTORS COMPRESSED USING VECTOR QUANTIZATION, by Jorge Sánchez, et al., U.S. Pub. No. 20120143853, published Jun. 7, 2012, entitled LARGE-SCALE ASYMMETRIC COMPARISON COMPUTATION FOR BINARY EMBEDDINGS, by Albert Gordo, et al.; and U.S. Pub. No. 20120158739, published Jun. 21, 2012, entitled SYSTEM AND METHOD FOR MULTIMEDIA INFORMATION RETRIEVAL, by Julien Ah-Pine, et al.

The following relate generally to methods for generation of representations of text data: U.S. Pub. No. 20100082615, published Apr. 1, 2010, entitled CROSS-MEDIA SIMILARITY MEASURES THROUGH TRANS-MEDIA PSEUDO-RELEVANCE FEEDBACK AND DOCUMENT RERANKING, by Stéphane Clinchant, et al., U.S. Pub. No. 20110137898, published Jun. 9, 2011, entitled UNSTRUCTURED DOCUMENT CLASSIFICATION, by Albert Gordo, et al.; and U.S. Pub. No. 20130204885, published Aug. 8, 2013, entitled DOCUMENT PROCESSING EMPLOYING PROBABILISTIC TOPIC MODELING OF DOCUMENTS REPRESENTED AS TEXT WORDS TRANSFORMED TO A CONTINUOUS SPACE, by Stéphane Clinchant, et al.

BRIEF DESCRIPTION

In accordance with one aspect of the exemplary embodiment, a method for diagnosis assistance includes receiving a request for a query from a requester, the query request including a new medical case. The new medical case is embedded in an embedding space in which a set of existing medical cases and a set of experts are embedded. Provision is made for the requester to select from a plurality of query types including a query-for-cases and a query-for-experts. When the query-for-cases is selected, a subset of the cases is returned, based on a computed similarity between the embedded new case and the embedded existing cases. When the query-for-experts is selected, a subset of the experts is returned, based on a computed similarity between the embedded new case and the embedded experts.

One or more of the steps may be performed with a computer processor.

In accordance with another aspect of the exemplary embodiment, a system for diagnosis assistance includes memory which stores instructions for receiving a request for a query from a requester, the query request including a new medical case; embedding the new medical case in an embedding space in which a set of existing medical cases and a set of experts are embedded; providing for the requester to select from a plurality of query types including a query-for-cases and a query-for-experts; when the query-for-cases is selected, returning a subset of the cases based on a computed similarity between the embedded new case and the embedded existing cases; and when the query-for-experts is selected, returning a subset of the experts based on a computed similarity between the embedded new case and the embedded experts. A processor in communication with the memory executes the instructions.

In accordance with another aspect of the exemplary embodiment, a method for diagnosis assistance includes, for each of an existing set of medical cases, generating a multidimensional representation in an embedding space. For each of a set of experts, a multidimensional representation in the embedding space is generated. A new case for which a diagnosis is sought is received. A multidimensional representation of the new case in the embedding space is generated. Provision is made for a plurality of query types, including a query-by-cases at a first cost and a query-by-experts at a second cost, higher than the first cost. When the query-by-cases is requested, a subset of the existing cases is identified, based on a similarity between the multidimensional representation of the new case and the multidimensional representations of existing cases in the set of cases. When the query-by-experts is requested, a subset of the experts is identified, based on a similarity between the multidimensional representation of the new case and the multidimensional representations of experts in the set of experts. Provision is also made for communicating the new medical case to one of the subset of experts for the expert to attempt to provide a diagnosis. A cost for the query is computed, based on the query type requested.

One or more of the steps may be performed with a computer processor.

DETAILED DESCRIPTION

The exemplary embodiment relates to a system and method for collaborative medical diagnosis in a social medical network for diagnosis assistance (SMNDA) or simply a "network." The system provides health workers with access to information to assist them in making a diagnosis by providing the ability to contact experts that are part of the network, while at the same time making better use of the limited time of the experts by encouraging users to contact experts only when other resources have not been useful, i.e., for truly challenging cases. The exemplary system provides a filtering mechanism which enables cases to be solved more efficiently and more quickly, thus making better use of the limited resources.

A requester submits a query request regarding a case for which a diagnosis is sought. A part or all of a new case may be used by the requester to query the system. In addition, the requester may submit a suggested diagnosis.

A "medical case," or simply a "case," as used herein, generally refers to any information about a specific medical problem in the form of one or more records. Each case is specific to a particular patient and a time frame over which the medical problem has been present, rather than the patient's entire medical records. A case may include information on a disease, medical condition, associated set of symptoms, or the like that have been generated by one or more health workers responsible for treating the patient. As an example, a case may include a collection of records that includes one or more text documents, such as descriptions of observations, such as symptoms, laboratory test results, patient monitoring results, such as results from EKG, blood pressure, and heart rate monitors, descriptions of prescribed medications and treatments, and/or one or more images, such as medical images, e.g., X-ray and other radiation images and photographic images of the patient, optionally associated with metadata, combinations thereof, and the like. The case may include a preliminary diagnosis based on observations. The case records may have been anonymized, for example by redacting some of the patient's personal information, such as the patient's name, address, and/or other information that the healthcare worker assembling the case information and/or the patient considers to be private.

A "requester," as used herein, generally refers to a person interacting with the system seeking assistance with diagnosis of a case. The requester may be a health worker, such as a nurse, medical doctor, dentist, radiologist, psychiatrist, veterinarian, other medical practitioner, or their employees, and in some cases may also be an expert in a particular field.

An "expert" is a health worker who is linked, by the system, to medical information, such as an expert profile and the expert's own cases, which can be queried based on a requester's case. The health worker may be required to register with the system in order to be considered an expert. In some embodiments, health workers may be required to provide evidence of their expertise (e.g., qualifications, minimum number of cases, etc.) in order to be classed as an expert. In other embodiments, any health worker can be established as an expert with the system simply by providing medical information, such as a set of cases and an expert profile.

A "user" of the system can be a requester, an expert, or both.

Figure 1:
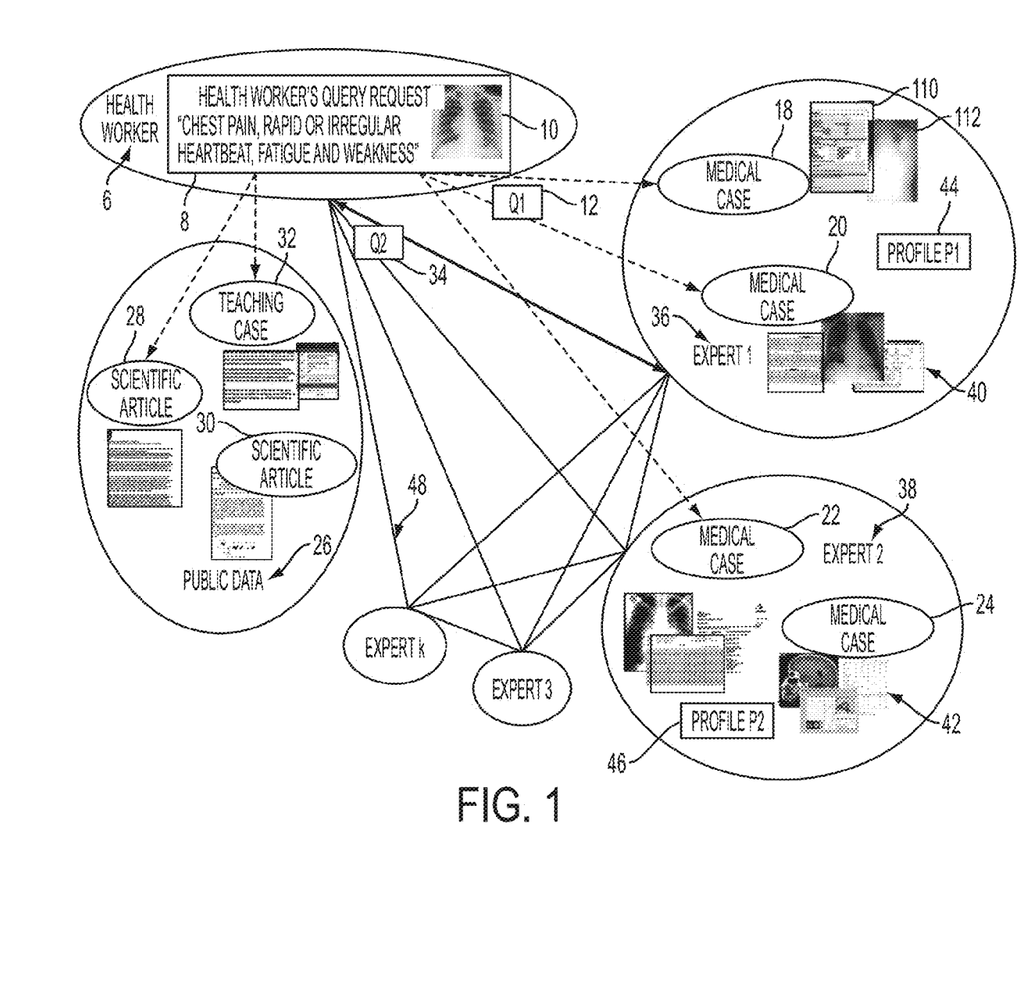
FIG. 1 is an illustrative overview of a Social Medical Network for Diagnostic Assistance (SMNDA) system.

As illustrated in FIG. 1, a requester 6, such as a health worker, generates a query request 8 related to a new medical case 10, which is to be used for performing a database query. The query to be performed is of one of a plurality of types, the types including a query-for-cases (QFC) and a query-for-experts (QFE). The two (or more) types of query may have different cost structures to encourage the requester to use the QFC search, at least initially. The query request 8 submitted by the health worker may be for a query Q1 12 of a first type, such as a QFC. For this type of query, the requester queries the system 14 (FIG. 2) and receives, in return, a list of medical cases such as one or more stored medical cases 18, 20, 22, 24, etc., which may be ranked from most relevant to least relevant to the query 12. The search results may have been generated by an automatic search of one or more databases. Additionally, the QFC query, or a separate query, may be used to search public data 26, which includes publicly-available documents, to retrieve responsive documents, such as illustrated documents 28, 30, 32, etc.

The requester is also able to submit a request 8 for a query Q2 34 of a second type, the query-for-experts (QFE), based on the information on the case 10. When the request for the second type of query is submitted, the system 14 searches for the experts which match the query. Each expert 36, 38, may be associated with a unique identifier through which the expert is linked to medical information 40, 42 associated with the expert, such as one or more of the medical cases 18, 20, 22, 24, etc. and a respective profile 44, 46. In some instances, two or more of the experts may be linked to a common medical case. However, in general, the experts have different sets of associated medical cases. The experts identified in the search are generally practitioners likely to be experts with respect to the queried case 10. The system returns one or more experts, e.g., a list of experts 36, 38, which may be ranked from most relevant to least relevant. The requester is able to select an expert to contact from the list proposed by the system. The requester pays for the query based on the type of query used. To encourage requesters to contact experts only when they consider it strictly necessary, a different cost is associated with the two types of queries. In particular, the cost C2 of a QFE is higher than the cost C1 of a QFC.

Figure 2:
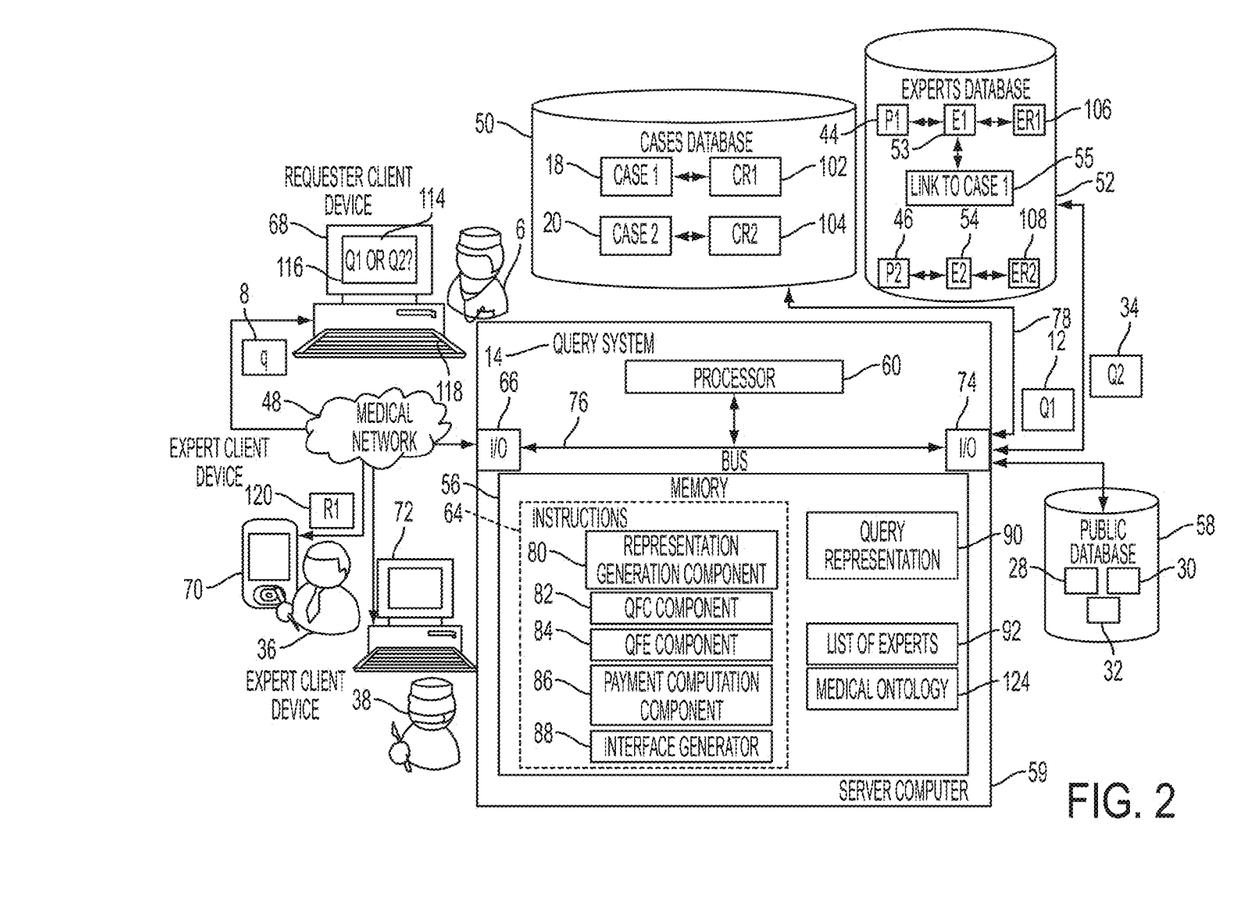
FIG. 2 is a functional block diagram of the SMNDA system in accordance with one embodiment.

The computer-implemented system 14 shown in FIG. 2 is capable of performing at least a part of the method described below with reference to FIG. 3. The system 14 is connected with health workers, such as requesters 6 and experts 36, 38, etc., through the private social medical network 48. The network 48 may connect heath workers at the level of a single hospital or over a wider network. In general, the health workers 6, 36, 38 can have different levels and types of expertise, such that at least some of the health workers are recognized by the system as being experts, in their respective fields. Through the system 14, the experts share their respective profiles 44, 46, etc., and can also share some of their anonymized medical cases 18, 20, 22, 24. These medical cases may contain records in a variety of forms, such as descriptions of symptoms, medical images, laboratory results, diagnoses, prescribed treatments, and the like, as noted above. The system 14 may put the requester in contact with a selected expert 36 or 38 through the private social medical network 48.

The medical cases 18, 20, 22, 24 may be stored in one or more cases databases 50. Similarly, one or more experts database(s) 52 or databases store(s) information relating to the experts 36, 38, etc. For example, for each expert 36, 38, etc. an associated unique identifier 53, 54 is linked to the expert's profile 44, 46 and to any other medical information related to the expert, such as the experts cases, which may be associated with the expert's identifier 53, 54 through links 55. The databases 50, 52 may be stored in system memory 56 and/or in remote memory accessible to the system. Additionally, the system 14 may have access to and be able to analyze the public documents 26 stored in one or more other medical databases (illustrated in FIG. 2 as a single public database 58 for convenience). Examples of such medical databases 58 may include one or more of:

a) those containing medical teaching cases from publicly available datasets, such as MyPACS, a free web application that allows radiologists to create their own online teaching file repositories by uploading medical images through their web browser (see, www.mypacs.net), EURORAD radiologic teaching files (see, www.eurorad.org), The American College of Radiology (ACR) database, CaseInPoint (see, http://3s.acr.org/CIP), and the Department of Pediatrics at the University of Florida database PediatricEducation (see, http://pediatrics.med.ufl.edu/education/);

b) pages of Wikipedia (where medical pages in many different languages are edited by experts and medical students, see, for example, N. COHEN, "Editing Wikipedia pages for Med School credit," New York Times, published online on Sep. 29, 2013);

c) collections of medical journals accessed through a common web portal (e.g., PubMed); and d) pages accessed through general search engines, such as Google pages. Through its Medical Condition and Symptom Search, for example, Google treats queries that appear to be medical symptoms in a special way showing a brief description of the condition, links to pages about the condition causes, symptoms, tests, treatment, prognosis and prevention and related searches from other users.

The embedding of a query case, existing case, or an expert is in the form of a multi-dimensional representation (a "signature"). In the exemplary embodiment, the cases 10, 18, 20, 22, 24, etc., experts (or more properly, the medical information 40, 42 associated with the experts 36, 38, etc.), and optionally, the public documents 28, 30, 32, etc., are embedded in a common search space in which distances between embeddings provide a meaningful measure of their similarity. As an example, a Euclidean space is used for embedding. This means that cases and experts can each be represented as a set of features, e.g., as a respective vector, and that their similarity can be measured using the Euclidean distance. Similar cases thus tend to be closer, in the embedding space, than dissimilar cases. Similar experts (e.g., practitioners with the same expertise) tend to be closer in the space than dissimilar experts. Additionally, experts tend to be closer in the space to the cases (of other experts) for which they themselves are an expert in the field than to cases for which they are not an expert, and vice versa. Various embedding techniques are described below.

The illustrated computer system 14 is hosted by one or more computing devices 59 and includes a processor 60, which controls the overall operation of the system 14 by execution of processing instructions which are stored in memory 56 connected to the processor 60. Memory 56 also stores instructions 64 for performing the exemplary method, which are implemented by the processor 60. Computer system 14 also includes a network interface 66, which is communicatively connected, via the network 48, with a set of client devices 68, 70, 72 operated by various authorized users 10, 36, 38, etc. of the system. The same or a separate interface(s) 74 connects the system 14 with databases 50, 52, 58. The various components of the computer 59 may be communicatively connected by a bus 76. Databases 50, 52, 58 may be linked to the system by wired or wireless links 78 or by network 48.

The instructions 64 include a representation generation component 80, a QFC component 82, a QFE component 84, a payment computation component 86, and an interface generator 88, which may be in the form of software and may be separate or combined. The representation component 80 generates a multi-dimensional representation 90 of a requester's query in the embedding space. If the requester has selected to perform only a QFC query, the QFC component 82 performs a QFC query based on the representation 90 generated by the representation generation component 80, and returns a list of cases whose representations are similar, in the embedding space, to the query representation and may also perform a search of the public database 58. The requester is then able to review these cases. If the requester has selected to perform only a QFE query, or has selected to perform both a QFC query and a QFE query, the QFE component 84 performs a QFE query based on the (same) representation 90 generated by the representation generation component 80 and returns a list 92 of those of the experts 36, 38 whose multi-dimensional representations of their medical information 40, 42 are similar, in the embedding space, to the query representation 90. The payment computation component 86 allocates a payment to be made by the requester using a differential cost structure which takes into account the type(s) of query(ies) made, the cost being lower for a QFC query than for a QFE query. The interface generator 88 communicates with the requester and experts' computing devices to receive instructions from the user/expert and present retrieved results.

Prior to performing the exemplary method, the cases 18, 20, 22, 24, etc. and the expert's medical information 40, 42 stored in the databases 50, 52 are each associated with a respective multi-dimensional representation. For example, as illustrated in FIG. 2, each case 18, 20 is associated with a respective multi-dimensional representation etc. 100, 102, denoted CR1, CR2, and each expert ID 53, 54, etc. is associated with a respective multi-dimensional representation 106, 108, denoted ER1, ER2, etc. Each multi-dimensional representation 100, 102, 106, 108 is derived from one or more records. In the case of a case signature 100, 102, the records pertain to the specific case, such as records 110, 112 for case 18 in FIG. 1. In the case of an expert, such as expert 36, the expert representation 106 may be derived from the expert's own profile 44 and optionally the one or more cases 18, 20 that are linked to the expert ID 36 (e.g., as represented by the case representations 100, 102 for these cases).

The interface generator 88 may be configured for generating a user interface 114 for display to a requester 6 on a display device 116 of the requester's computing device 68. For example, a thin client may be installed in memory of the computing device 68 for generating the user interface. The user interface may provide for uploading a case 10 to the system, selecting the type of query to be performed, annotating retrieved documents, and the like. The user may interact with the user interface 114 via a user input device 118, such as a keyboard, keypad, touch or writable screen, or the like. The processor of computing device 68 communicates the requester's case 10 and other instructions to the system and receives instructions from the system for displaying retrieved data.

The computer system 59 may include one or more computing devices, such as a PC, such as a desktop, a laptop, palmtop computer, portable digital assistant (PDA), server computer, cellular telephone, tablet computer, pager, combination thereof, or other computing device capable of executing instructions for performing the exemplary method.

The memory 56 may represent any type of non-transitory computer readable medium such as random access memory (RAM), read only memory (ROM), magnetic disk or tape, optical disk, flash memory, or holographic memory. In one embodiment, the memory 56 comprises a combination of random access memory and read only memory. In some embodiments, the processor 60 and memory 56 may be combined in a single chip. Memory 56 stores instructions for performing the exemplary method as well as the processed data. The digital processor 60 can be variously embodied, such as by a single-core processor, a dual-core processor (or more generally by a multiple-core processor), a digital processor and cooperating math coprocessor, a digital controller, or the like.

The network interface 66, 74 allows the computer to communicate with other devices via a computer network, such as a local area network (LAN) or wide area network (WAN), or the internet, and may comprise a modulator/demodulator (MODEM) a router, a cable, and and/or Ethernet port.

Computing devices 68, 70, 72 may be similarly configured to the server computer 59, with memory, a processor, and a network interface (not shown).

The term "software," as used herein, is intended to encompass any collection or set of instructions executable by a computer or other digital system so as to configure the computer or other digital system to perform the task that is the intent of the software. The term "software" as used herein is intended to encompass such instructions stored in storage medium such as RAM, a hard disk, optical disk, or so forth, and is also intended to encompass so-called "firmware" that is software stored on a ROM or so forth. Such software may be organized in various ways, and may include software components organized as libraries, Internet-based programs stored on a remote server or so forth, source code, interpretive code, object code, directly executable code, and so forth. It is contemplated that the software may invoke system-level code or calls to other software residing on a server or other location to perform certain functions.

Figure 3:
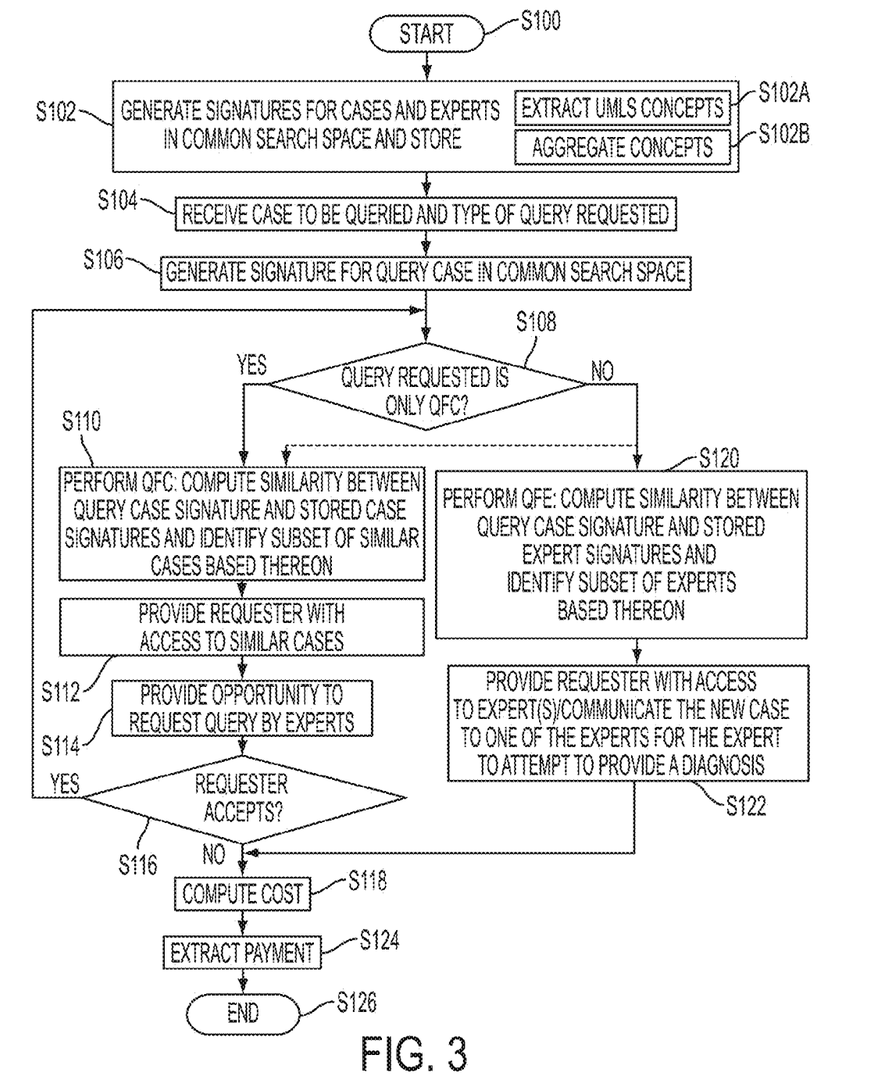
FIG. 3 is a flow chart which illustrates a method for providing diagnostic assistance in accordance with another aspect of the exemplary embodiment.

FIG. 3 illustrates a method for performing the exemplary querying method. The method begins at S100.

At S102, for each of a set of existing, stored cases 18, 20, 22, 24, etc., and for each of a set of experts 36, 38, etc., a respective multi-dimensional representation 102, 104, 106, 108 is generated, in the common embedding space, e.g., with the representation generation component 80. Each expert is associated with only one multi-dimensional representation. The multi-dimensional representations generated may be stored in the databases 50, 52, or in system memory 56. As will be appreciated, this step may be performed by a separate computing device and/or updated at intervals, e.g., when new cases are added to the database 50 and/or when an expert updates his or her profile and/or creates links 55 between new or different cases and the expert's personal identifier 36.

At S104, a requester 6 submits query request 8 to the system 14, which is received and stored in memory 56. The query request includes a new medical case 10 for which a diagnosis is sought. The new case can include one or more optionally anonymized case records 110, 112. The case records may include descriptions of symptoms, lab results, medical images, etc., as noted above. In addition the requester may provide a proposed diagnosis, if a confirmation is being sought. The requester may request that a QFC, QFE or both be performed. For example, a user interface 116 is generated on the client device which asks the requester whether the system should perform a QFC or a QFE (or both). The requester inputs a selection and the selection is received by the system. In other embodiments, the system may automatically perform a QFC first. In some embodiments, the requester may be required to be a member of the network before submitting a query request. In other embodiments, the requester may be permitted to use the query-by-cases search functionality without joining the network.

At S106, a query representation 90, which is representative of the data in the user's query case 10, is generated by the representation component 80 by embedding the query case 10 into the same search space as was used for embedding the cases and the experts' information.

At S108, the system 14 determines whether the requester has requested a query-for-cases, a query-for-experts, or both.

If the user has selected a QFC, at S110, the representation 90 is used by the QFC component 82 to perform a first query 12 of the stored cases by computing a measure of similarity between the representation 90 and the case representations 102, 104 stored at S102 (for a cost C1). The QFC 12 may be performed in the database 50 of the system or in the external databases 58, or in both. A subset of the most similar case representations is identified.

The case(s) corresponding to the similar case representation(s) is/are identified and may be ranked in order of representation similarity. For example, the QFC component 82 may rank cases based on the similarity of their representation to the query representation and return the top-K results and/or only results whose similarity exceeds a predetermined threshold.

At S112, a subset of relevant cases 18, 20, 22 is returned to the requester 6. For example, the requester 6 is provided with a list of the identified cases or otherwise provided with access to the cases and the records that they contain as well as any documents retrieved from public databases, e.g., via the user interface 114. In some embodiments, the system 14 may perform a multimodal document clustering with diversity seeking and/or perform query-specific multi-document summarization to reduce the amount of time needed for the requester to parse the retrieved information. See, for example, J. Ah-Pine, et al., "Comparison of several combinations of multimodal and diversity seeking methods for multimedia retrieval," Multilingual Information Access Evaluation II. Multimedia Experiments, Lecture Notes in Computer Science, vol. 6242, pp 124-132 (2010); C. R. Chowdary, et al., "Esum: an efficient system for query-specific multi-document summarization," ECIR (Advances in Information Retrieval), pp. 724-728 (2009); C. Shen, "Multi-Document Summarization via the Minimum Dominating Set," COLING, pp. 984-992 (2010); A. Haghighi, et al., "Exploring Content Models for Multi-Document Summarization," ACL 2009 Optionally, specific visualization techniques can be used to assist the requester in browsing through the retrieved documents. See, for example, Christian Tominski et al., "TimeViz Browser—A Visual Survey of Visualization Techniques for Time-Oriented Data" (Nov. 28, 2013).

The requester 6 may provide relevance feedback to the system 14. For example, the requester can identify those of the returned existing cases which appear more relevant than others and may annotate the retrieved case records and/or other retrieved documents which he or she considers more relevant to the current case 10, e.g., by highlighting the parts that are considered more useful by the requester. If the requester found enough information to solve the case 10, the requester may decide to share his anonymized medical case 10 together with his diagnosis and proposed/implemented treatments and the case is stored in the case database 50. The medical case can contain a list of links to the documents 28, 30, 32 (with the corresponding annotations) that helped the health worker making the decision. If the requester is also registered with the system as being an expert, the new case 10 may be linked to the expert's ID.

At S114, the requester may be given the opportunity to request a QFE. The subsequent QFE is at a cost C2.

If at S116, the requester accepts, for example, because the returned cases have not provided sufficient information to allow the requester to diagnose the query case 10, the method returns to S108, otherwise, to S118.

If at S108, the system determines that the requester has requested a query for experts, then at S120, a QFE 34 is performed, by the QFE component 84, by computing the similarity between the representation 90 and the expert representations 106, 108. A set of the most similar, expert representations is identified. Optionally, a query-for-cases is also performed, if not already done. As will be appreciated, the query-for-cases and query-for-experts may be performed with exactly the same query representation 90. Alternatively, the representation used for QFE may be a refined version of the QFC which uses the relevance feedback. For example, the cases retrieved by the system and deemed relevant by the requester in the QFC stage can be added to the QFE query and the modified representation 90 then reflects these added documents.

At S122, the experts corresponding to the similar stored expert representations are identified and may be ranked in order of representation similarity and/or based on other criteria. The QFE component 84 returns the top-K most relevant experts and/or only those experts whose relevance is above a given threshold.

The requester 6 may be provided with the list of experts or otherwise provided with access to one or more of the experts. The requester can retrieve more information about each expert (e.g., access his or her profile 44, 46) and can choose an expert to contact. The system may then communicate the new 8 case to one of the subset of experts for the expert to attempt to provide a diagnosis. For example, the system may send a help request 120, such as an email message, SMS, telephone message, combination thereof, or the like, to the expert. The message may include or provide a link to the requester's case 10 so that the expert can review the documents and any tentative diagnosis suggested by the requester. In another embodiment, the requester may be provided with information for contacting the expert directly.

If the selected expert accepts the request to help the requester, the system may provide the expert with access to the documents that were retrieved and organized/annotated by the requester, in case the expert wants to gain additional insight. The expert can also decide not to view these documents. The expert may also obtain the annotations from the requester. The expert may also be provided with information about the requester, such as the requester's profile, which may identify a communication protocol (e.g., email address, chat, audio or video-conference through the social network) that allow the expert to contact the requester in order to ask further questions, request additional documents, and to provide help. The expert may then attempt to provide a diagnosis and communicate the diagnosis to the requester. There is no guarantee, of course, that the expert will be successful in the diagnosis.

If the selected expert refuses the invitation to help, the next expert on the list 92 may be contacted by the system. For example, if the first expert attempted to diagnose the case but was unable to do so, or lacks the time to do so, the first expert notifies the system and the next expert can be contacted. An expert who tried to help but is not sure about her/his diagnoses can also add notes, annotation to the query with the aim of attracting attention to certain details and guide the next expert(s) to key points.

At S118 a cost is computed, by the payment computation component 86. The cost depends on whether the requester requested a QFC or QFE (or both). If the user has first performed a QFC, the QFE cost C2 may include at least part or all the cost C1 of the QFC, so that the requester is not unduly penalized for performing a QFC first.

The payment time may be predefined. The cost C2 may be charged when querying for experts, when contacting an expert, or when receiving a diagnosis. In the first case, if an expert refuses or cannot help, the system allows the user to contact other experts until an expert agrees to answer. In the second case, the cost is charged only if the expert accepts the request to help the user. In the third case, payment is not due unless a diagnosis is made.

At S124, the computed cost is assigned to the requestor and a payment is extracted by the payment computation component 86. For example, the payment may be automatically transferred from the requester's account to the system and any payments due to the expert are allocated to the expert who reviewed the case 10 and provided a diagnosis.

The method ends at S126.

The method illustrated in FIG. 3 may be implemented in a computer program product that may be executed on a computer. The computer program product may comprise a non-transitory computer-readable recording medium on which a control program is recorded (stored), such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other non-transitory medium from which a computer can read and use. The computer program product may be integral with the computer 59, (for example, an internal hard drive of RAM), or may be separate (for example, an external hard drive operatively connected with the computer 59), or may be separate and accessed via a digital data network such as a local area network (LAN) or the Internet (for example, as a redundant array of inexpensive of independent disks (RAID) or other network server storage that is indirectly accessed by the computer 59, via a digital network).

Alternatively, the method may be implemented in transitory media, such as a transmittable carrier wave in which the control program is embodied as a data signal using transmission media, such as acoustic or light waves, such as those generated during radio wave and infrared data communications, and the like.

The exemplary method may be implemented on one or more general purpose computers, special purpose computer (s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like. In general, any device, capable of implementing a finite state machine that is in turn capable of implementing the flowchart shown in FIG. 3, can be used to implement the diagnosis method. As will be appreciated, while the steps of the method may all be computer implemented, in some embodiments one or more of the steps may be at least partially performed manually.

Further details of the system and method will now be described.

Embedding (S102)

The medical cases and experts (as represented by their associated information 40, 42) are embedded in a common Euclidean space. To be able to establish a similarity score, the query case 10 (the case records 110, 112), the cases 18, 20, 22, 24, and the experts are all represented in a unique homogeneous form, e.g., as a multidimensional vector 90, 102, 104, 106, 108, where each element (dimension) of the vector corresponds to a respective medical-related concept. Each case may be represented by an aggregate of the representations of the records (or parts of records) of which it is composed or directly from the concepts identified therein. Similarly, each expert may be represented by an aggregate of the representations of the cases to which he or she is linked or directly from the concepts identified therein, and/or based on other information 40, 42 associated with the expert, such as his profile 44, 46. The various representations are generated using the same set of concepts.

In the exemplary embodiment, each representation 90, 102, 104, 106, 108 is generated using a medical ontology 124 of biomedical concepts. The ontology may include at least 1000 concepts, or at least 100,000 concepts, or at least 1 million concepts, each concept corresponding to a respective dimension in the representation, i.e., the multidimensional representations may include at least 1000 dimensions, prior to any dimensionality reduction. The ontology 124 may include different types of concepts that are linked together. As example, the concepts may include parts and sub-parts of the human body, biological functions, diseases, syndromes, and other medical conditions, pharmacological substances, including general classes of medicines and specific examples of medicines, and other methods of treatment, and the like. As an example ontology, the Unified Medical Language System (UMLS, see http://www.nlm.nih.gov/research/umls/) designed by the US National Library of Medicine, may be employed. See, for example, Olivier Bodenreider, "The Unified Medical Language System (UMLS): integrating biomedical terminology," Nucleic Acids Research, 32, D267-D270 (2004). UMLS is a standard medical nomenclature which includes multiple levels, some of which are available for a fee. The level 0 subset, which is available free of charge, contains over 1.8 million concepts and 17 million relations between these concepts. Such an ontology 124 can be used to represent a record, or element of the record, based on information extracted from the record, and similarly for queries, cases, and experts. The record, case, or expert can then be indexed by its respective representation(s).

Figure 4:
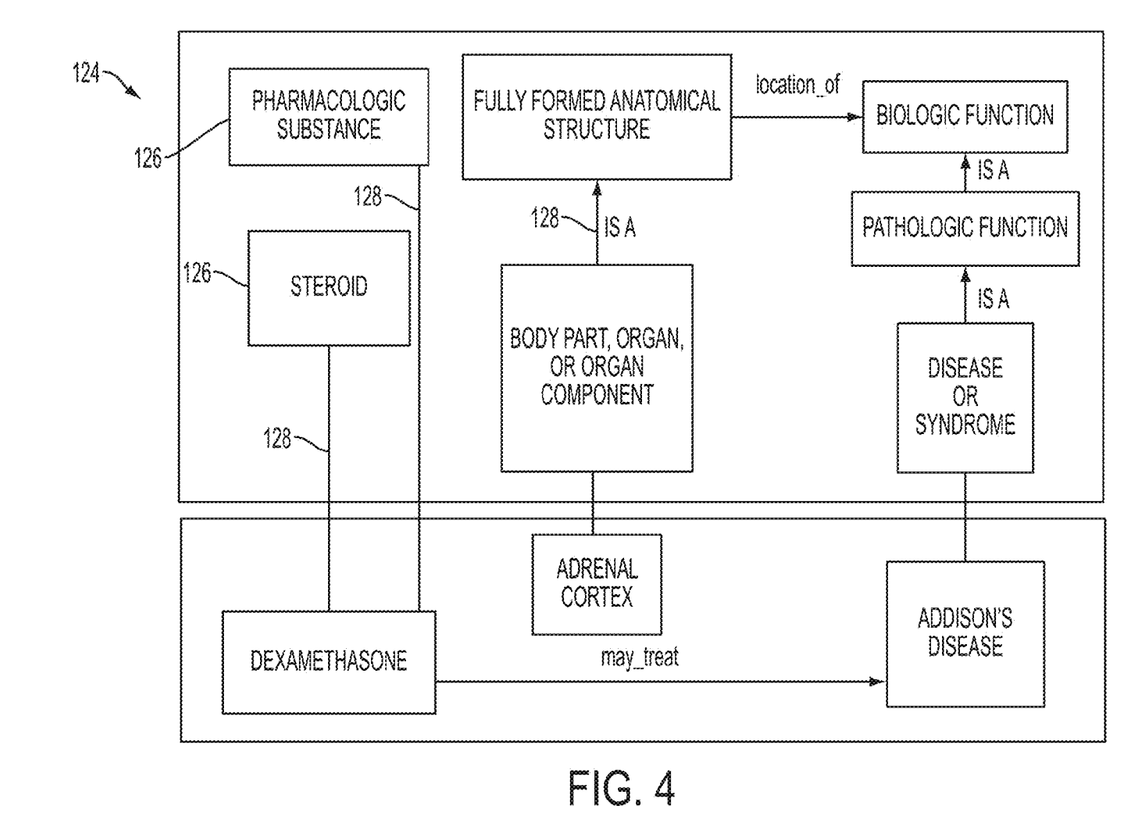
FIG. 4 is a schematic view of part of a medical ontology.

FIG. 4 illustrates a small portion of the knowledge represented in the UMLS-based ontology 124 with different types of relationships. The ontology includes a set of concepts 126, represented in FIG. 4 as blocks. Relationships between the concepts 126 are represented by links 128, shown here as arrows and lines. The arrows denote specific types of relationships, such as may_treat, is_a, and location_of. Lines indicate subset-type links between concepts of different levels. The concepts that are less specific (higher level concepts) may be less useful and thus may be excluded from consideration in generating the representation. For example, the high level concepts "fully-formed anatomical structure" and "biological function" may be ignored. In other embodiments, all the concepts in the ontology (at any given time, since the exemplary ontology is not static) may be used in generating the representation.

In some embodiments, at least some of the medical concepts 126 selected from the ontology for use in generating the representations may each be associated with a set of terms, such as synonyms (e.g., different names for a given drugs, Latin names for parts of the body, common and medical names for diseases, and other medical conditions, and expressions of medical conditions that strongly correlate with them). Each record may also be associated with a set of terms, e.g., derived from the metadata of the record or using other extraction methods, optionally, with a measure of occurrence of the term, such as a frequency of its occurrence in the record. When a term (or set of terms) corresponding to a concept's term is found in one of the records, the corresponding concept can be recognized, and the matching concept represented by a value in the representation of the record, sometimes with a confidence score.

Additionally, the links 128 between concepts can be used to identify related concepts which can be used in generating the representation of the record, with directly linked and parent (higher level) concepts being more relevant than concepts which are more remote from an identified concept. In one embodiment, a concept that is related to a concept that matches a term in the record may thus be represented in the representation of the record by propagating at least some confidence level to the related concept.

Embedding Records, Cases, and Documents

A medical case 18, 20, query 12, 34, or public document 28, 30, 32 may contain multiple elements. These elements can be considered together as forming a single element, however the case can also be separated into several sub-parts (several elements). Therefore in what follows, the term "medical object" (or simply "object") can refer to any one of an entire medical case, a record of the case, an expert, a query, an item of public data, such as a published article, web page, etc., subpart(s) thereof, and combinations thereof.

The medical object can be of the same or different modalities, such as images with related textual and/or audio reports, referring to the same medical case (e.g., a congestive heart failure or a brain aneurism). In the exemplary method, each medical object (e.g., health record, case, expert, query) is represented as a vector of UMLS concepts 126 where:

1: Each dimension corresponds to the unique ID of a UMLS concept (e.g., [C0001175] is the ID for the concept "Acquired Immunodeficiency Syndrome" and [C0002372] is the ID for the concept "Aluminum Hydroxide Gel")

2: The corresponding value of the dimension may provide information about the relevance of the concept with respect to the object. In one embodiment, the value can be a scalar which ranges, for example, from 0-1. In other embodiments the value is binary, e.g., 1 if relevant, 0 if not. In some embodiments, weights are used to express confidence that the concept is relevant or not.

Building such a vector representation can be performed as follows:

S102A. The set of UMLS concepts is first extracted from the medical object(s), possibly with a set of weights (confidence values).

S102B. The extracted ontology concepts (and weighted confidence values) are then aggregated at the object level.

There are different ways to extract the UMLS concepts from a medical object (S102A), which may depend, in part on the type of object. For example, some medical objects may have been manually coded with UMLS terms at the time of their creation, e.g., by a practitioner, an administrative person, or automatically, e.g., by a system designed to add the relevant UMLS terms when creating the original medical object, or can appear as MESH keywords in medical journals. Medical objects may have keywords and free text attached to their content as metadata, or the content itself can be unstructured text (for example doctors' notes, the content of the article).

The exemplary representation generation component 80 may include a natural language parser which extracts nouns and multi-word expressions from the text portions of the medical objects. An exemplary parser is the Xerox Incremental Parser (XIP) which is described, for example, in U.S. Pat. No. 7,058,567, issued Jun. 6, 2006, entitled NATURAL LANGUAGE PARSER, by Aït-Mokhtar, et al.; Aït-Mokhtar, S., Chanod, J-P., Roux, C. "Robustness beyond Shallowness: Incremental Deep Parsing". Natural Language Engineering 8 (2002) 121-144. Similar incremental parsers are described in Aït-Mokhtar "Incremental Finite-State Parsing," Proc. 5th Conf. on Applied Natural Language Processing (ANLP'97), pp. 72-79 (1997), and Aït-Mokhtar, et al., "Subject and Object Dependency Extraction Using Finite-State Transducers," Proc. 35th Conf. of the Association for Computational Linguistics (ACL'97) Workshop on Information Extraction and the Building of Lexical Semantic Resources for NLP Applications, pp. 71-77 (1997). The syntactic analysis performed by the parser may include the construction of a set of syntactic relations (dependencies) from an input text by application of a set of parser rules. Exemplary methods are developed from dependency grammars, as described, for example, in Mel'čuk I., "Dependency Syntax," State University of New York, Albany (1988) and in Tesnière L., "Elements de Syntaxe Structurale" (1959), Klincksiek, Eds. (Corrected edition, Paris 1969).

A specific application of the XIP parser to the medical field, which may be utilized herein, is described in Hagège, C., et al., "Linguistic and Temporal Processing for Discovering Hospital Acquired Infection from Patient Records," Proc. Knowledge Representation for Health-Care (KR4HC), ECAI 2010, Lisbon, Portugal, August 2010, Lecture Notes in Computer Science, Volume 6512, pp. 70-84, Springer Berlin/Heidelberg (2011), hereinafter, "Hagège 2010", and in "Assistant de Lutte Automatisée et de Détection des Infections Nosocomiales à partir de Documents textuels Hospitaliers (ALADIN-DTH), Development Of An Automated Assistant to Monitor Hospital Acquired Infections and a Detection System for Hospital Acquired Infections from Patient Discharge Summaries, at http://www.aladin-project.eu/index-en.html) hereinafter "ALADIN-DTH." These last two references provide methods for extraction of named entities, particularly medical terms, which can be compared with the concepts to determine if there is a match.

The terms in the documents corresponding to UMLS concepts are identified and used to update the dimensions of the representation of the medical object. The concepts (dimensions of the representation) can be weighted using weighting schemes, such as term frequency-inverse document frequency (TF-IDF) or C-value/NC-value. See, Frantzi, K., et al., "Automatic Recognition of Multi-Word Terms: the C-value/NC-value Method," Intern'l J. Digital Libraries, 3 (2) 115-130 (August 2000) for details of this method. These methods allow the frequency of occurrence of the terms corresponding to the concepts to be taken into account either as a value in the feature vector or as a confidence measure used to weight the value in the representation of the medical object.

For each text-based medical object (e.g., medical report, treatment, prescription, etc.) a text-based representation of the document may be generated, which can be a Bag-of-Words (Concepts) representation. In one embodiment, only those concepts that have confidence scores above a given threshold, or the top N concepts, based on their confidence scores, are retained.

Medical objects that have no or limited metadata (e.g., medical images), can be automatically tagged with UMLS concepts using pre-trained classifiers (e.g., at the document level). These classifiers are trained on annotated medical data. For example, for images and scanned documents, a visual content-based statistical representation can be generated based on low level features extracted from patches of the image, such as color or gradient features. As examples of such statistical representations, a Bag-of-Visual Words or a generative model-based representation, such as a Fisher Vectors-based representation, may be used. See, for example, U.S. Pub. Nos. 2007005356, 20070258648, 20080069456, 20100092084, 20100098343, 20100189354, 20110026831, 20110091105, 20110137898, 20120045134, 20120076401, and 20120143853, the disclosures of which are incorporated herein by reference in their entireties, for methods of generating representations of images which may be used herein to assign concepts to an image. The statistical representation is input to the trained classifier which outputs a confidence score for each concept. As with the text-based concept representations, in one embodiment, only those concepts that have confidence scores above a given threshold, or the top N concepts, based on their confidence scores are retained.

The UMLS concepts which have been extracted may then be pooled into a vector representation of the medical object (S102B), as follows:

In the case where no weight or confidence value is associated with the extracted UMLS concepts, the vector can be binary to indicate the presence of absence of a concept in the object. It can also have integer values in the case of a histogram of counts. It can have floating point values in the case where the histogram of counts is normalized, e.g., by the total number of counts (frequency histogram).

In the case where a weight or confidence value is associated to the extracted UMLS concepts, the counts can be weighted with such values (this is referred to sum or average pooling). In another embodiment, for each UMLS concept, the maximal confidence value in the considered medical object can be selected (this is referred to as max pooling).

Where multidimensional representations of two or more sub-parts of a medical object are generated, these may be aggregated to form a representation of the medical object as a whole or maintained separately.

Each medical object can then be indexed according to the dimensions of the vector having a non-zero value. Medical cases which are already in the system need only to be indexed once. Using this method, the query, which can also include a set of records including images and lab results, is also transformed into a similar representation as for the medical objects in the database. For public documents retrieved for one requester from the public dataset, the index may be stored. This caching system avoids computing the index of the corresponding documents again for other requesters.

Embedding Experts

To embed an expert (which can be any health worker) in the same space as queries, public documents, and stored cases, a set of UMLS concepts is associated with the expert and these concepts aggregated into a bag-of-concepts representation. A set of UMLS concepts can be associated to an expert using one or more of the following:

1. Concepts may be determined from the profile 44, 46, e.g., based on degrees, certifications, and/or registrations of the professional.

2. Concepts may be determined using the classification of the coded medical procedures which have been performed by the professional over the past years. In the US, several coding schemes are used, such as the Healthcare Common Procedure Coding System (HCPCS). The ICD-10 Procedure Coding System (ICD-10-PCS) is an international system of medical classification used for procedural coding. In France, the classification is referred to as "codage des actes médicaux." Hence, if a coded act is associated to one or multiple UMLS concepts (or to concepts in another ontology), then a profile may be encoded as the histogram of coded medical procedure counts.

3. Concepts may be mined from the publications authored by the expert.

4. Concepts may be extracted from the medical cases that are linked to the expert.

Different weights may be provided, in the expert's representation, to concepts extracted for these different sources of information. For example, more weight may be attributed to concepts extracted from the expert's cases than from articles authored by the expert. While a UMLS-based representation is used in the exemplary embodiment for embedding all medical objects, other representations are contemplated. For example, probability vectors, as described in US 20100312798, may be computed based on a given set of predefined criteria, such as condition data, event-specific data, demographic data, clinical data, medical history, family history, social history, diagnosis history, and treatment history.

Matching in the Embedded Space (S110, S120)

To compute the similarity between two UMLS-based vectorial representations (e.g., case-to-case matching or case-to-expert), a simple measure such as the Hamming distance (in the case of a binary representation), the dot-product, the Euclidean distance, or the cosine distance can be used. However, since the UMLS vectors tend to be very sparse (for example, at level 0, UMLS already contains 1.8 million concepts), these measures may not be too effective.

One solution to the sparsity problem is to project the data into a lower-dimensional space where the representation is denser, e.g., by performing a Singular Value Decomposition (SVD) or a Probabilistic Latent Semantic Analysis (PLSA) on the vectors. Following dimensionality reduction, one of the simple similarity measures can then be applied in the lower-dimensional space, e.g., a Euclidean distance.

Another approach is to keep the sparse representation but to define measures between vectors which can relate different UMLS dimensions. For example, it may be assumed that the "proximity" between two concepts i and j can be measured and that it has a value Pij. Then, the matrix of proximities P for all the concepts can be used to define a similarity measure x'Py between two UMLS vectors x and y, where x represents the query and y represents the case, expert, or document representation being compared, or vice versa. x' represents the transpose of vector x.

In some embodiments, a normalized similarity measure is obtained as follows:

$$\frac{x'Py}{\sqrt{x'Px}\sqrt{y'Py}}$$

where y' represents the transpose of vector y.

To define measures of proximity Pij between UMLS concepts, a measure of the similarity between concepts can be determined. The similarity between two concepts X and Y measures "how much is X like Y"? This can be measured using the distance between the concepts in a hierarchy of concepts where the link between a parent and a child denotes a "is-a" relationship. For example, a direct link between two concepts is used to denote a high measure of proximity, whereas concepts that are spaced by two or more links, with other concepts in between them, are accorded a lower measure of proximity. For example, proximity Pij may be a function of the inverse of the number of links, optionally with concepts that are more distant than, for example, two or three links, being assigned a zero or a low proximity.

Another measure of proximity may be based on the relatedness between concepts. The relatedness between two concepts X and Y measures "how much is X related to Y"? There several possible relatedness relationships between concepts including "is-a", "part-of", "treats", "affects", "symptom-of", etc. As an example, while "tetanus" and "deep cut" are two related concepts, they are not similar (similar concepts are related but related concepts are not necessarily similar). Several similarity and relatedness measures have been proposed and compared in the literature. See, for example, Ted Pedersen, et al., "Measuring the Similarity and Relatedness of Concepts in the Medical Domain: IHI 2012 Tutorial (2012), hereinafter "Pedersen 2012", accessible at http://www.comp.hkbu.edu.hk/ihi2011/Documents%20-%20web2011IHI_files/IHI2012-semantic-similarity-tutorial.pdf; Siddharth Patwardhan, et al., "Using WordNet-based Context Vectors to Estimate the Semantic Relatedness of Concepts," Proc. EACL 2006 Workshop on Making Sense of Sense: Bringing Computational Linguistics and Psycholinguistics Together, Trento, Italy, pp. 1-8 (2006); Pedersen, T., et al., "Measures of Semantic Similarity and Relatedness in the Biomedical Domain," J. Biomedical Informatics 40: 288-299 (2007). Simple software packages exist to measure such quantities (see, Pedersen 2012). One or more of these relatedness/similarity measures can be used to generate a proximity value for each pair of concepts in the UMLS hierarchy.

A potential issue with using a proximity matrix P to propagate similarity values to other, similar concepts is that the full matrix P may be too large to store and manipulate. One solution to this includes storing, in a sparse format, only those values Pij which are above a predetermined threshold. Another solution includes computing the Pij terms on-the-fly. Since the vectors x and y are generally very sparse, very few terms need to be computed on-the-fly. In some embodiments, the proximity matrix P may be pre-computed and stored.

Once similarity measures, such as scores, have been computed between the query case 10 and each representation of a stored medical object (e.g., case, document, or expert) with which it is being compared, the stored medical object can be ranked based on the similarity measures. A subset of the medical objects is then retrieved, based on the ranking, i.e., fewer than all medical objects. For example, the top N most highly ranked medical objects, based on the computed similarity metric between the vectors, can be retrieved. In another embodiment, only those medical objects which meet a threshold on the similarity measure are retrieved.

As will be appreciated, any suitable measure may be employed for computing similarity between UMLS concepts and the method is not limited to those suggested herein.

When matching a case and an expert, other criteria may be taken into account to rank experts, beyond vector similarity. These criteria may include one or more of:

1. The availability of the expert: an expert can configure his/her account in the social medical network to indicate whether the expert is currently available or to indicate a maximum number of cases s/he is willing to consider within a particular time period 2. Ratings provided by other health workers who previously received help from the same expert.

3. The number of "followers" in the social network. Users of the system may be permitted to request notifications when the expert updates his or her profile, authors an article, or modifies the linked set of cases. These users may be classed as followers.

In some embodiments, a rule-based diagnostic detection system, such as that described in US Pub. No. 20130179176, may be integrated into the filtering step.

Differentiated Cost (S118)

As noted above, a cost is associated with queries to the system and different costs are associated with the two different types of queries. The QFC query is assigned a lower cost than a QFE query. The payment extracted for the QFE query may be contingent on other factors, such as whether there is an expert on the list who is willing to review the requester's case and provide a diagnosis. The payments for the QFC and QFE queries may be made in a real or a virtual currency and/or in another form of remuneration, such as credits to use the system for future queries. Some or all of the payment for a QFE query may be credited to the expert providing the case review and/or diagnosis. In some cases, the QFC query may be free, or paid for as part of a membership subscription to the medical network.

Having different cost structures encourages the requester to use the QFC query first, but does not prevent the requester from going straight to a QFE query, or having both performed simultaneously, for example, if the medical case needs an urgent diagnosis.

In one embodiment, the cost may be a virtual cost, expressed in virtual money, which is only usable in the system. The virtual money may be spent by issuing queries to the system, the cost of a query-for-experts C2 being significantly higher than the cost of a query-for-cases C1. This is to encourage users to solve their cases by themselves and only to contact experts when this is needed (since experts are a rare resource). In one embodiment, the cost of a query-for-cases is null.

Different mechanisms can be implemented for users of the system to earn and/or use virtual money. As examples:

1. Each subscriber initially receives credits when they join the network. Different subscribers might receive a different amount of credit. For example, health workers who work for public, philanthropic, and/or Non-Governmental Organizations (NGOs) may receive a larger number of credits than others, and/or the costs C1 and C2 may be different for different users.

2. A user may earn credits if he or she contributes to the database of cases with his or her own (anonymized) cases.

3. When an expert helps with a case, that expert may earn credit. This is to encourage experts to help others since, in return, they will also get help. Also, the amount of credits may be a function of the rating of the user who received the help.

4. A user may earn credit based on effort, e.g., time, spent on a case. When the requester queries for a case, the system can record how many of the returned cases and/or documents are viewed by the requester or how much time is spent viewing each case/document. This is a measure of the willingness of the requester to solve the problem by him or herself and can be encouraged by awarding credits accordingly.

5. Virtual credits may be bought with standard money.

In another embodiment, rather than performing the two types of queries sequentially, a single query may be performed that retrieve both cases (and documents) and experts simultaneously. The retrieval interface would show the retrieved cases and experts separately. In such a case, a cost would not be incurred when querying the system but when accessing the cases and/or experts. Again, a differentiated cost structure is provided, with the cost of accessing an expert being higher than the cost of accessing a case. However, a disadvantage with this embodiment is that since both cases and experts are retrieved simultaneously, the requester may be more tempted to contact an expert directly rather than to trying to make a diagnosis by him or herself.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A method for diagnosis assistance comprising:
    receiving a request for a query from a requester, the query request including a new medical case;
    embedding the new medical case in an embedding space in which a set of existing medical cases and a set of experts are embedded;
    providing for the requester to select from a plurality of query types including a query-for-cases and a query-for-experts;
    when the query-for-cases is selected, returning a subset of the cases based on a computed similarity between the embedded new case and the embedded existing cases; and
    when the query-for-experts is selected, returning a subset of the experts based on a computed similarity between the embedded new case and the embedded experts
    wherein at least one of the embedding, providing, returning the subset of the cases, returning the subset of the experts, and computing the query cost are performed with a computer processor.

2. The method of claim 1, further comprising computing a cost for the query, the cost for a query-for-experts being different from the cost for a query-for-cases.

3. The method of claim 2, wherein the computed query cost is higher for a query-for-experts than for a query-for-cases.

4. The method of claim 1, wherein the embedding of the new medical case in the embedding space comprises computing a multidimensional representation of the medical case based on a medical ontology, the embedding of the existing medical cases and the set of experts being also based on the medical ontology.

5. The method of claim 4, wherein the medical ontology comprises a set of medical concepts joined by links, and wherein each of the medical concepts corresponds to a respective dimension in the representation.

6. The method of claim 5, wherein the computing the similarity measure between the representation of the new case and representations of the existing cases or experts, a matrix of proximities is applied to the multidimensional representation of the new case that accounts for relationships between concepts in the ontology.

7. The method of claim 4, wherein the ontology includes parts of the human body, biological functions, medical conditions, pharmacological substances, and combinations thereof.

8. The method of claim 4, wherein the medical ontology is based on the Unified Medical Language System.

9. The method of claim 1, wherein the experts in the set of experts are each embedded based on information associated with the expert selected from the group consisting of:
    a profile of the expert;
    coded medical procedures which have been performed by the expert;
    articles authored by the expert;
    stored medical cases linked to the expert; and
    combinations thereof.

10. The method of claim 1, wherein when the query-for-experts is selected, the returning of the subset of the experts is also based on at least one of:
    an availability of the expert;
    a rating of the expert; and
    a number of followers of the expert among users of the system.

11. The method of claim 1, further comprising, when the query-for-cases is selected, returning documents from a public database based on a computed similarity between the embedded new case and documents embedded in the embedding space.

12. The method of claim 1, wherein when the query-for-experts is selected, providing the new case to a selected one of the subset of experts for formulating a diagnosis.

13. The method of claim 12, wherein when the query-for-experts is selected, providing for making a payment to the expert for formulating the diagnosis.

14. The method of claim 1, wherein the new medical case comprises a plurality of records relating to a specific patient.

15. The method of claim 1, wherein the plurality of records comprises records selected from the group consisting of laboratory test results, images, descriptions of symptoms, results of patient monitors, diagnoses, prescribed medications and treatments, and combinations thereof.

16. The method of claim 1, further comprising when the query-by-cases is selected, providing for a query-by-experts to be performed subsequent to the query-by-cases.

17. A system comprising memory storing instructions for performing the method of claim 1 and a processor in communication with the memory for executing the instructions.

18. A computer program product comprising a non-transitory recording medium storing instructions, which when executed on a computer causes the computer to perform the method of claim 1.

19. A system for diagnosis assistance comprising:
    memory which stores instructions for:
        receiving a request for a query from a requester, the query request including a new medical case;
        embedding the new medical case in an embedding space in which a set of existing medical cases and a set of experts are embedded;
        providing for the requester to select from a plurality of query types including a query-for-cases and a query-for-experts;
        when the query-for-cases is selected, returning a subset of the cases based on a computed similarity between the embedded new case and the embedded existing cases; and
        when the query-for-experts is selected, returning a subset of the experts based on a computed similarity between the embedded new case and the embedded experts;
        computing a cost for the query, the cost for a query-for-experts being different from the cost for a query-for-cases; and a processor in communication with the memory for executing the instructions.

20. A network comprising a system for diagnosis assistance and a set of user devices for linking requesters and experts with the system, the system comprising:
memory which stores instructions for:
receiving a request for a query from a requester, the query request including a new medical case;
embedding the new medical case in an embedding space in which a set of existing medical cases and a set of experts are embedded;
providing for the requester to select from a plurality of query types including a query-for-cases and a query-for-experts;
when the query-for-cases is selected, returning a subset of the cases based on a computed similarity between the embedded new case and the embedded existing cases; and
when the query-for-experts is selected, returning a subset of the experts based on a computed similarity between the embedded new case and the embedded experts; and
a processor in communication with the memory for executing the instructions.

21. The system of claim 20 wherein the instructions further comprise instructions for computing a cost for the query, the cost for a query-for-experts being different from the cost for a query-for-cases.

22. A method for diagnosis assistance comprising:
for each of an existing set of medical cases, generating a multidimensional representation in an embedding space;
for each of a set of experts, generating a multidimensional representation in the embedding space;
receiving a new case for which a diagnosis is sought;
generating a multidimensional representation of the new case in the embedding space;
providing for a plurality of query types, including a query-by-cases at a first cost and a query-by-experts at a second cost, higher than the first cost;
when the query-by-cases is requested, identifying a subset of the existing cases based on a similarity between the multidimensional representation of the new case and the multidimensional representations of existing cases in the set of cases;
when the query-by-experts is requested, identifying a subset of the experts based on a similarity between the multidimensional representation of the new case and the multidimensional representations of experts in the set of experts, and providing for communicating the new case to one of the subset of experts for the expert to attempt to provide a diagnosis; and
computing a cost for the query based on the query type requested.

* * * * *